(12) United States Patent
Hyun et al.

(10) Patent No.: US 9,377,420 B2
(45) Date of Patent: Jun. 28, 2016

(54) THERMAL CONDUCTIVITY MEASURING DEVICE

(71) Applicant: ELECTRONICS AND TELECOMMUNICATIONS RESEARCH INSTITUTE, Daejeon (KR)

(72) Inventors: Younghoon Hyun, Seoul (KR); Young Sam Park, Daejeon (KR); Moon Gyu Jang, Daejeon (KR); Taehyoung Zyung, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 14/861,909

(22) Filed: Sep. 22, 2015

(65) Prior Publication Data

US 2016/0011131 A1    Jan. 14, 2016

Related U.S. Application Data

(62) Division of application No. 13/780,166, filed on Feb. 28, 2013, now Pat. No. 9,170,223.

(30) Foreign Application Priority Data

Jul. 3, 2012   (KR) .................... 10-2012-0072351
Oct. 22, 2012  (KR) .................... 10-2012-0117228

(51) Int. Cl.
*G01N 25/18*   (2006.01)
*G01K 1/00*    (2006.01)

(52) U.S. Cl.
CPC .................................. *G01N 25/18* (2013.01)

(58) Field of Classification Search
USPC ..................... 374/44, 208, 166, 112, 183
See application file for complete search history.

(56) References Cited

U.S. PATENT DOCUMENTS 3,263,485 A * 8/1966 Mahmoodi ............ G01N 25/18
                                              374/112
3,521,476 A    7/1970 Day Ralph K
(Continued)

OTHER PUBLICATIONS

Allon I. Hochbaum et al., "Enhanced thermoelectric performance of rough silicon nanowires", Nature, Jan. 10, 2008, pp. 163-167, vol. 451, No. 10.
(Continued)

*Primary Examiner* — Mirellys Jagan
(74) *Attorney, Agent, or Firm* — Rabin & Berdo, P.C.

(57) ABSTRACT

The inventive concept relates to a thermal conductivity measuring device. The thermal conductivity measuring device may include a first structure which is connected to one side end of a sample and receives heat from a heat source; a second structure connected to the other side end of the sample; a first stage connected to the first structure while supporting the first structure; a second stage connected to the second structure while supporting the second structure; a connection unit connected between the first stage and the second stage; and a measuring unit measuring temperatures of the first and second structures and the first and second stages. Since the thermal conductivity measuring of the inventive concept correct a temperature change of a stage due to heat transmission emitted from the stage considering a measurement environment, reliability of measurement may be improved.

4 Claims, 6 Drawing Sheets

(56) References Cited

U.S. PATENT DOCUMENTS

| | | | |
|---|---|---|---|
| 3,733,887 A | 5/1973 | Stanley et al. | |
| 5,005,985 A | 4/1991 | Piorkowska-Galeska et al. | |
| 5,667,301 A * | 9/1997 | Jurkowski | G01N 33/442 374/43 |
| 5,940,784 A * | 8/1999 | El-Husayni | G01N 25/005 374/43 |
| 6,116,777 A * | 9/2000 | Pause | G01N 25/18 374/43 |
| 6,142,662 A | 11/2000 | Narh et al. | |
| 6,331,075 B1 | 12/2001 | Amer et al. | |
| 6,896,405 B2 * | 5/2005 | Osone | G01N 25/18 374/43 |
| 7,445,379 B2 | 11/2008 | Chang | |
| 8,628,237 B1 * | 1/2014 | Liu | G01N 25/18 374/120 |
| 2006/0045165 A1 * | 3/2006 | Chan | G01N 3/60 374/43 |
| 2014/0309242 A1 | 10/2014 | Chen et al. | |

OTHER PUBLICATIONS

Akram I. Boukai et al., "Silicon nanowires as efficient thermoelectric materials", Natures, Jan. 10, 2008, pp. 168-171, vol. 451, No. 10.

* cited by examiner

THERMAL CONDUCTIVITY MEASURING DEVICE

CROSS-REFERENCE TO RELATED APPLICATIONS

This is a Divisional of U.S. application Ser. No. 13/780,166, which was filed on Feb. 28, 2013, and allowed on Jun. 29, 2015, claims the benefit of priority under 35 U.S.C. §119 of Korean Patent Application No. 10-2012-0072351, filed on Jul. 3, 2012, and Korean Patent Application No. 10-2012-0117228, filed on Oct. 22, 2012, the entire contents of which are hereby incorporated by reference.

BACKGROUND

The present inventive concept herein relates to thermal conductivity and a method of measuring the thermal conductivity.

A thermoelectric device includes a thermoelectric generator device converting a thermal energy into an electrical energy and a thermoelectric cooling device converting an electrical energy into a thermal energy. The thermoelectric generator device can reuse a waste thermal energy and thereby it is used in various fields of a vehicle, a spacecraft, a semiconductor circuit, etc.

As standards of thermoelectric performance of the thermoelectric device, a figure of merit (hereinafter, it is referred to as ZT) is used. To develop a thermoelectric device having superior thermoelectric performance, a material having a high ZT has to be developed. However, since variables determining ZT has correlation, it is difficult to develop the thermoelectric device having superior thermoelectric performance only by using a simple bulk material. Thus, recently, a thin film, a nano wire material, etc. using a nano-based technology are being studied.

As a nano-based technology is applied, the importance of method of measuring thermal conductivity and thermal conductance has increased. Since temperature changes of both sides of nano-based materials are minute as compared with a conventional bulk material, it is difficult to measure thermal conductivity and thermal conductance of the nano-based material.

SUMMARY

Embodiments of the inventive concept provide a thermal conductivity measuring device. The thermal conductivity measuring device may include a first structure which is connected to one side end of a sample and receives heat from a heat source; a second structure connected to the other side end of the sample; a first stage connected to the first structure while supporting the first structure; a second stage connected to the second structure while supporting the second structure; a connection unit connected between the first stage and the second stage; and a measuring unit measuring temperatures of the first and second structures and the first and second stages. The measuring unit calculates thermal conductivity of the sample using the measured temperatures of the first and second structures and the first and second stages, and the amount of heat provided from the heat source.

Embodiments of the inventive concept also provide a thermal conductivity measuring method. The thermal conductivity measuring method may include providing heat to a first structure connected to one side end of a sample; measuring temperatures of the first structure and a second structure connected to the other side end of the sample; measuring temperatures of a first stage supporting the first structure and a second stage supporting the second structure; and calculating thermal conductivity of the sample using the amount of heat provided to the first structure and the measured temperatures of the first structure, the second structure, the first stage and the second stage.

BRIEF DESCRIPTION OF THE FIGURES

Preferred embodiments of the inventive concept will be described below in more detail with reference to the accompanying drawings. The embodiments of the inventive concept may, however, be embodied in different forms and should not be constructed as limited to the embodiments set forth herein. Rather, these embodiments are provided so that this disclosure will be thorough and complete, and will fully convey the scope of the inventive concept to those skilled in the art. Like numbers refer to like elements throughout.

DETAILED DESCRIPTION OF THE EMBODIMENTS

Figure 1:
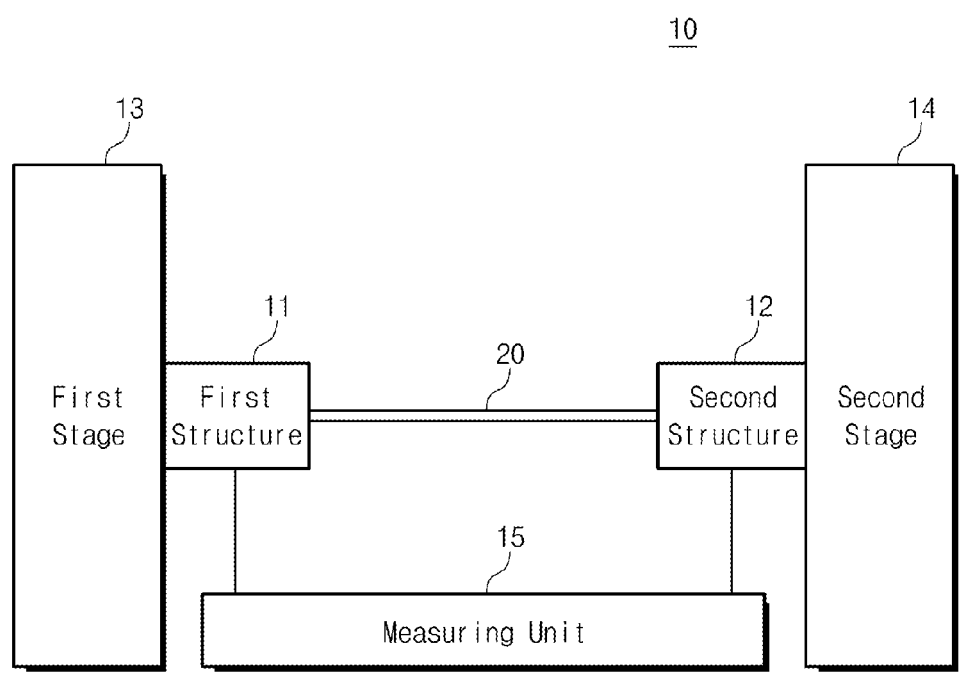
FIG. 1 is a block diagram illustrating a thermal conductivity measuring device.

Embodiments of inventive concepts will be described more fully hereinafter with reference to the accompanying drawings, in which embodiments of the invention are shown. This inventive concept may, however, be embodied in many different forms and should not be construed as limited to the embodiments set forth herein. Rather, these embodiments are provided so that this disclosure will be thorough and complete, and will fully convey the scope of the inventive concept to those skilled in the art. In the drawings, the size and relative sizes of layers and regions may be exaggerated for clarity. Like numbers refer to like elements throughout.

FIG. 1 is a block diagram illustrating a thermal conductivity measuring device. Referring to FIG. 1, a thermal conductivity measuring device 10 includes a first structure 11, a second structure 12, a first stage 13, a second stage 14 and a measuring unit 15. The thermal measuring device 10 measures thermal conductivity of a sample 20 connected between the first structure 11 and the second structure 12.

The first structure 11 is thermally connected to one side end of the sample 20 and the first stage 13. When measuring thermal conductivity, the first structure 11 is heated by a heat source. The heated first structure 11 transmits heat to the sample 20.

The first stage 13 is a support body for supporting the first structure. The first stage 13 may include an insulation part for blocking out thermal leakage. The first stage 13 has a large thermal capacity as compared with the first structure 11 and the sample 20. Thus, heat being transmitted from the first structure 11 to the first stage 13 is smaller than heat being transmitted from the first structure 11 to the sample 20. It can be assumed that a temperature of the first stage 13 is not changed by heat being transmitted.

The second structure 12 is thermally connected to the other side end of the sample 20 and the second stage 14. When measuring thermal conductivity, the second structure 12 receives heat from the first structure 11 through the sample 20.

The second stage 14 is a support body for supporting the second structure 12. The second stage 14 may include an insulation part for blocking out thermal leakage. The second stage 14 has a large thermal capacity as compared with the second structure 12 and the sample 20. Thus, heat being transmitted from the second structure 12 to the second stage 14 is smaller than heat being transmitted from the sample 20 to the second structure 12. It can be assumed that a temperature of the second stage 14 is not changed by heat being transmitted.

The measuring unit 15 is electrically connected to the first structure 11 and the second structure 12. The measuring unit 15 measures calories being provided to the first structure 11 and a temperature change of the first and second structures 11 and 12. The measuring unit 15 can calculate thermal conductivity of the sample 20 using a measured value.

However, in case of measuring the nano-based sample 20 having a small a cross sectional area, heat being transmitted from the first structure 11 to the sample 20 may become small. As heat being transmitted from the first structure 11 to the sample 20 becomes small, a measurement error may occur by heat being transmitted from the first structure 11 to the first stage 13.

Figure 2:
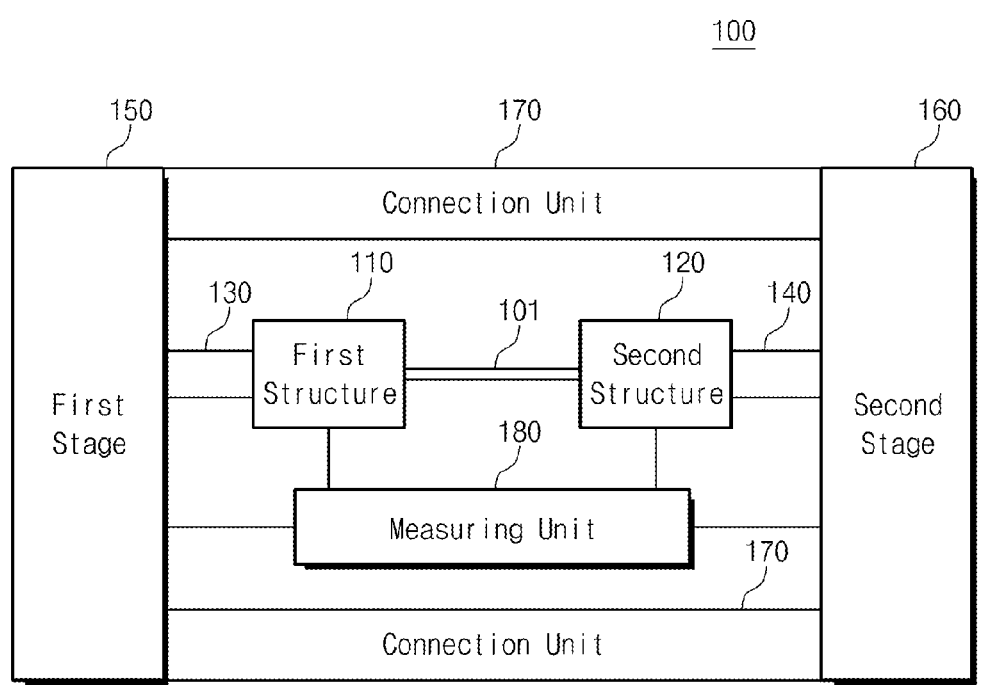
FIG. 2 is a block diagram illustrating an improved thermal conductivity measuring device in accordance with some embodiments of the inventive concept.

FIG. 2 is a block diagram illustrating an improved thermal conductivity measuring device in accordance with some embodiments of the inventive concept. Referring to FIG. 2, a thermal conductivity measuring device 100 includes a first structure 110, a second structure 120, a third structure 130, a fourth structure 140, a first stage 150, a second stage 160, a connection unit 170 and a measuring unit 180.

The thermal conductivity measuring device 100 measures thermal conductivity of a sample 101 connected between the first structure 110 and the second structure 120. The thermal conductivity measuring device 100 calculates thermal conductivity by measuring not only a temperature change of the first and second structure 110 and 120 but also a temperature change of the first and second stages 150 and 160. Thus, the thermal conductivity measuring device 100 can correct an error of thermal conductivity calculation process due to heat being transmitted from the first and second structures 110 and 120 to the first and second stages 150 and 160 and heat being transmitted between the first and second stages 150 and 160.

The first structure 110 is connected to one side end of the sample 101 and the third structure 130. When measuring thermal conductivity, the first structure 110 is heated by receiving heat from an external heat source. A method that the external heat source provides heat to the first structure 110 is not limited. For instance, the external heat source can heat the first structure 110 in the form of an electromagnetic wave or an ultrasonic wave. The electromagnetic wave may be light, laser or a FR wave. However, it is an illustrative and the inventive concept is not limited thereto. The heated first structure 110 transmits the sample 101 and the third structure 130.

The second structure 120 is connected to the other side end of the sample 101 and the fourth structure 140. The second structure 120 receives heat from the sample 101 and transmits heat to the fourth structure 140.

The third and fourth structures 130 and 140 are structures for connecting the first and second structures 110 and 120 to the first and second stages 150 and 160. The third and fourth structures 130 and 140 may be formed in a beam form. The third and fourth structures 130 and 140 support the first and second structures 110 and 120 in the air to prevent heat from being transmitted from the first and second structures 110 and 120 in a direction other than the sample 101. The third and fourth structures 130 and 140 reduce the amount of heat being transmitted from the first and second structures 110 and 120 to the first and second stages 150 and 160.

The first stage 150 is connected to the first structure 110 through the third structure 130. The first stage 150 is a support body for supporting the first structure 110. The first stage 150 may include an insulation part for blocking out thermal leakage. The first stage 150 receives heat from the heated first structure 110 through the third structure 130.

The second stage 160 is connected to the second structure 120 through the fourth structure 140. The second stage 160 is a support body for supporting the second structure 120. The second stage 160 may include an insulation part for blocking out thermal leakage. The second stage 160 receives heat from the sample 101 through the fourth structure 140. Since the second stage 160 has a large thermal capacity, it can be assumed that heat being transmitted from the first structure 110 to the second stage 160 through the sample 101 and the second structure 120 cannot change a temperature of the second stage 160.

The connection unit 170 seals up the space between the first and second stages 150 and 160 to make the inside of the thermal conductivity measuring device 100 become a vacuum state. For instance, the inside of the thermal conductivity measuring device 100 may have the degree of a vacuum of the range of $10^{-1}$~$10^{-9}$ torr. That is, the connection unit 170 and the first and second stages 150 and 160 place the first through fourth structures 110~140 in a space of the vacuum state to reduce heat being leaked from the first through fourth structures 110~140 to outside.

The connection unit 170 connects between the first and second stages 150 and 160 to form a thermal path between the first and second stages 150 and 160. Thus, when measuring thermal conductivity, heat may be transmitted from the first stage 150 to the second stage 160 through the connection unit 170. A temperature of the first stage 150 may be changed by the heat transmitted from the first stage 150 to the second stage 160.

The measuring unit 180 measures temperature changes of the first structure 110, the second structure 120, the first stage 150 and the second stage 160. The measuring unit 180 measuring a thermal capacity being provided from the outside to the first structure 110. The measuring unit 180 can calculate thermal conductivity of the sample 101 using a measured value. A temperature measuring method of the measuring unit 180 is not limited. For instance, the measuring unit 180 includes a temperature measuring sensor, a temperature measuring camera, a thermocouple or a thermistor to measure a temperature.

In FIG. 2, the measuring unit 180 is illustrated as one block connected to the first structure 110, the second structure 120, the first stage 150 and the second stage 160. However, this is only as an illustration and a structure of the measuring unit 180 is not limited thereto. For example, the measuring unit 180 may be separated to be included in each of the structures and each of the stages. The measuring unit 180 may be attached to the outside of the thermal conductivity measuring device 100.

Figure 3:
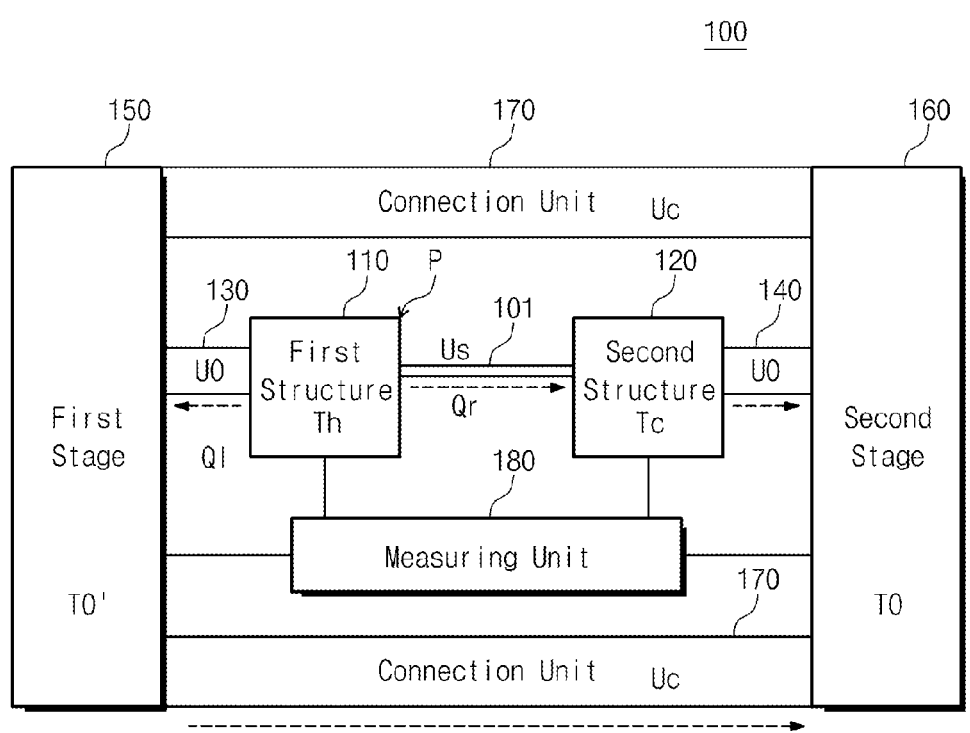
FIG. 3 is a block diagram for explaining a thermal conductivity measuring method of the thermal conductivity measuring device of FIG. 2.

Since the thermal conductivity measuring device 100 measures temperature changes of not only the structures 110 and 120 but also the stages 150 and 160, the thermal conductivity measuring device 100 can correct errors due to heat being transmitted from the structures 110 and 120 to the stages 150 and 160 and heat being transmitted between the stages 150 and 160. With reference to FIG. 3, the thermal conductivity measuring method in accordance with the inventive concept will be described in more detail.

FIG. 3 is a block diagram for explaining a thermal conductivity measuring method of the thermal conductivity measuring device 100 of FIG. 2. A thermal conductivity measuring device of FIG. 3 is the same as the thermal conductivity measuring device of FIG. 2.

In the thermal conductivity measuring device of FIG. 3, it is assumed that thermal conductance of the sample 101 is Us, thermal conductance of the third and fourth structures 130 and 140 is U0 and thermal conductance of the connection unit 170 is Uc. The thermal conductance is a value obtained by dividing a heat transfer rate of material by a temperature difference of both sides of the material. The heat transfer rate is the amount of thermal energy flowing through the material per hour. The thermal conductance has a reciprocal value of thermal resistance for conduction.

When measuring thermal conductivity, heat P per hour is provided to the first structure 110 by an external heat source. Heat Qr per hour is transmitted from the first structure 110 to the second stage 160 through the sample 101, the second structure 120 and the fourth structure 140. Heat Q1 per hour is transmitted from the first structure 110 to the first stage 150. If ignoring heat which leaks to the outside, the heat P, a relation of the heat Qr and the heat Q1 may be expressed as a mathematical formula 1.

$$P = Qr + Q1 \quad \text{[mathematical formula 1]}$$

It is assumed that a temperature of the first structure 110 heated by a heat source is Th, a temperature of the second structure 120 to which heat is transmitted through the sample 101 is Tc, a temperature of the first stage 150 heated by the first structure 110 is T0' and a temperature of the second stage 160 is T0. Since the heat Qr is heat transmitted per hour from the first structure 110 to the second stage 160 via the second structure 120, the heat Qr may be expressed as a mathematical formula 2 using a heat transfer equation.

$$Qr = (Th - T0)\frac{U0Us}{U0 + Us} \quad \text{[mathematical formula 2]}$$

Similarly, since the heat Q1 is heat transmitted per hour from the first structure 110 to the second stage 160 via the first stage 150, the heat Q1 may be expressed as a mathematical formula 3.

$$Q1 = (Th - T0)\frac{U0Uc}{U0 + Uc} \quad \text{[mathematical formula 3]}$$

If organizing the mathematical formulas 1, 2 and 3, the heat P being provided to the first structure 110 per hour is expressed as a mathematical formula 4.

$$P = (Th - To)\left(\frac{U0Us}{U0 + Us} + \frac{U0Uc}{U0 + Uc}\right) \quad \text{[mathematical formula 4]}$$

Referring to the mathematical formula 4, a temperature difference (Th−T0)/P (hereinafter it is referred to as Sh) between the first structure 110 and second stage 160 with respect to the heat being provided to the first structure 110 per hour is expressed as a mathematical formula 5.

$$Sh = \frac{(U0 + Us)(U0 + Uc)}{U0(Us(U0 + Uc) + Uc(U0 + Us))} \quad \text{[mathematical formula 5]}$$

Since heat being transmitted from the first structure 110 to the second structure 120 through the sample 101 is the same as the heat being transmitted from the second structure 120 to the second stage 160 through the fourth structure 140, a mathematical formula 6 comes into existence.

$$Us(Th - Tz) = U0(Tc - T0) \quad \text{[mathematical formula 6]}$$

Referring to the mathematical formulas 6 and 4, a temperature difference (Tc−T0)/P (hereinafter it is referred to as S1) between the second structure 120 and the second stage 160 with respect to the heat provided to the first structure 110 per hour is expressed as a mathematical formula 7.

$$S1 = \frac{Us(U0 + Uc)}{U0(Us(U0 + Uc) + Uc(U0 + Us))} \quad \text{[mathematical formula 7]}$$

Since heat being transmitted from the first structure 110 to the first stage 150 through the third structure 130 is the same as the heat being transmitted from the first stage 150 to the second stage 160 through the connection unit 170, a mathematical formula 8 comes into existence.

$$U0(Th - T0') = Uc(T0' - T0) \quad \text{[mathematical formula 8]}$$

Referring to the mathematical formulas 8 and 4, a temperature difference (T0'−T0)/P (hereinafter it is referred to as Sc) between the first stage 150 and the second stage 160 with respect to the heat provided to the first structure 110 per hour is expressed as a mathematical formula 8.

$$Sc = \frac{U0(U0 + Us)}{U0(Uc(U0 + Us) + Us(U0 + Uc))} \quad \text{[mathematical formula 9]}$$

If organizing the mathematical formulas 5, 7 and 9, like a mathematical formula 10, the thermal conductance Us of the sample 101 can be expressed as a formula including Sh, S1 and Sc.

$$Us = \frac{S1}{(Sh - S1)(Sh + S1 - Sc)} \quad \text{[mathematical formula 10]}$$

The Sh, the S1 and the Sc are experimental values that can be experimentally measured using the measuring unit 180. Thus, using the mathematical formulas described above, the thermal conductivity measuring device 100 can calculate the thermal conductance Us on the basis of values measured in the measuring unit 180.

If assume that thermal conductivity of the sample 101 is Ks, a cross sectional area of the sample 101 is As and a length of the sample 101 is Ls, the thermal conductivity Ks is expressed as a mathematical formula 11.

$$Ks = \frac{UsLs}{As} \qquad \text{[mathematical formula 11]}$$

If applying the mathematical formula 10 to the mathematical formula 11, like a mathematical formula 12, the thermal conductivity Ks of the sample 101 can be expressed as a formula including Sh, S1 and Sc.

$$Ks = \frac{S1Ls}{(Sh - S1)(Sh + S1 - Sc)As} \qquad \text{[mathematical formula 12]}$$

As described above, according to the thermal conductivity measuring method of the inventive concept, thermal conductance and thermal conductivity of the sample 101 can be calculated by using temperatures of the first structure 110, the second structure 120 and the first stage 150. The thermal conductivity measuring method of the inventive concept considers not only temperature changes of the first and second structures 110 and 120 but also a temperature change due to thermal conductivity of the first stage 150. Thus, since an error due to the thermal conductivity of the first stage 150 can be corrected, reliability of the measurement can become high.

Figure 4:
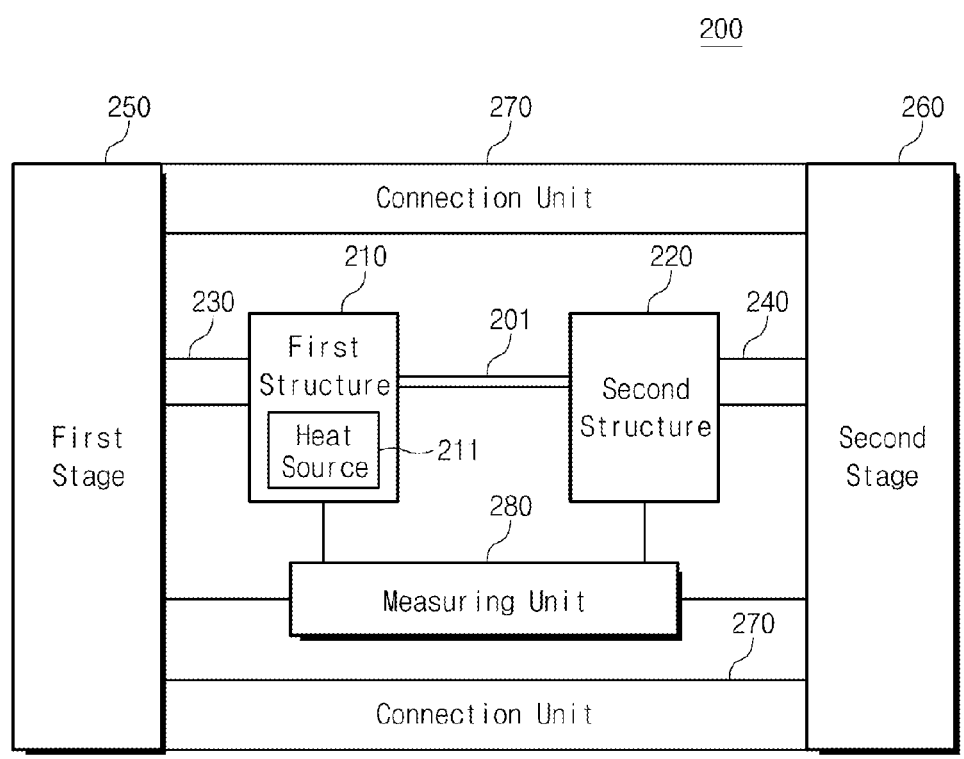
FIG. 4 is a block diagram illustrating an improved thermal conductivity measuring device in accordance with further embodiments of the inventive concept.

FIG. 4 is a block diagram illustrating an improved thermal conductivity measuring device 200 in accordance with further embodiments of the inventive concept. Referring to FIG. 4, the thermal conductivity measuring device 200 includes a first structure 210, a second structure 220, a third structure 230, a fourth structure 240, a first stage 250, a second stage 260, a connection unit 270 and a measuring unit 280.

Constituent elements except the first structure 210 of the thermal conductivity measuring device 200 of FIG. 4 have the same constituent and operation as those of the thermal conductivity measuring device 100. Unlike the first structure 110 of FIG. 3, the first structure 210 of FIG. 4 does not receive heat from the outside but includes a heat source 211 providing heat.

The heat source 211 is physically connected to the first structure 210 to provide heat to the first structure 210 when measuring thermal conductivity. The heat source 211 may be located inside the first structure 210. The heat source 211 may be attached to a surface of the first structure 210. A method that the heat source 211 provides heat to the first structure 210 is not limited. For instance, the heat source 211 can heat the first structure 210 using a Joule heating. For the Joule heating, the heat source 211 may include a metal material.

The thermal conductivity measuring device 200 heats the first structure 210 using the internal heat source 211 and measures temperature changes of the first and second structures 210 and 220 and the first and second stages 150 and 160. Since the thermal conductivity measuring device 200 considers not only a temperature change of the first and second structures 210 and 220 but also a temperature change due to thermal conduction of the first stage 250, reliability of the measurement becomes high.

Figure 5:
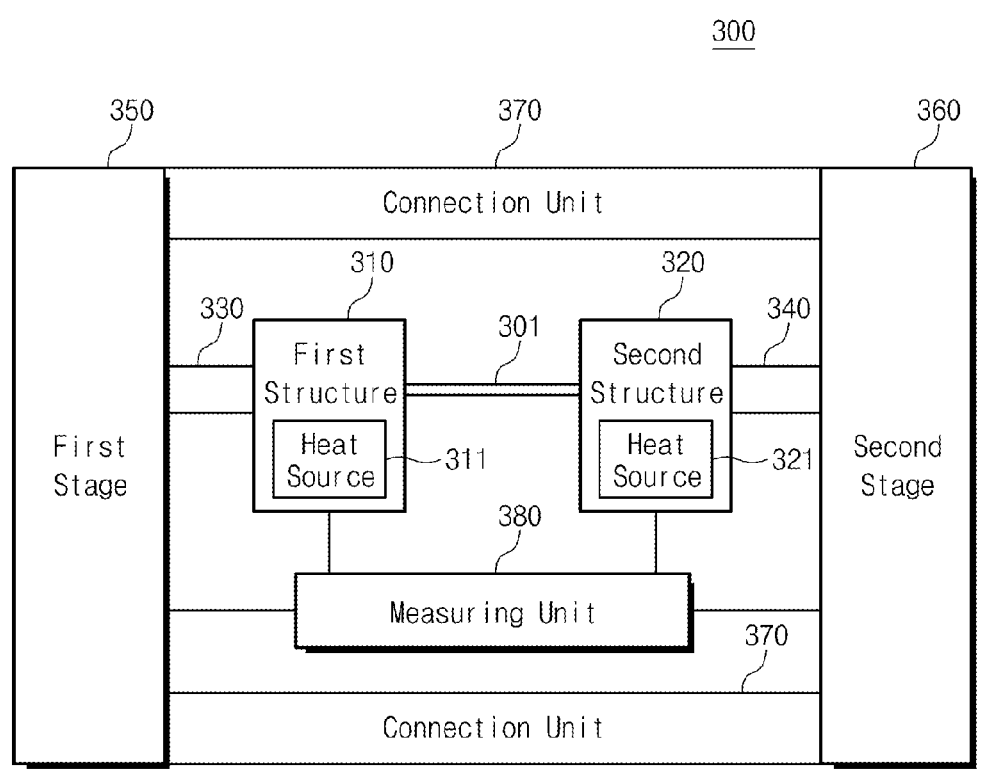
FIG. 5 is a block diagram illustrating an improved thermal conductivity measuring device in accordance with still further embodiments of the inventive concept.

FIG. 5 is a block diagram illustrating an improved thermal conductivity measuring device 300 in accordance with still further embodiments of the inventive concept. Referring to FIG. 5, the thermal conductivity measuring device 300 includes a first structure 310, a second structure 320, a third structure 330, a fourth structure 340, a first stage 350, a second stage 360, a connection unit 370 and a measuring unit 380.

The thermal conductivity measuring device 300 may provide heat to not only the first structure 310 but also the second structure 320. The thermal conductivity measuring device 300 can calculate thermal conductivity of a sample 301 by measuring heat provided to the first and second structures 310 and 320 and temperature changes of the first and second structures 310 and 320 and the first and second stages 350 and 360.

The first structure 310 includes a heat source 311. The second structure 320 includes a second heat source 321. The first and second heat sources 311 and 321 can independently provide heat to the first and second structures 310 and 320 respectively. For instance, the first heat source 311 and the second heat source 321 can selectively operate. The measuring unit 380 can measure temperature changes of the first and second structures 310 and 320 and the first and second stages 350 and 360 several times in response to operations of the first and second heat sources 311 and 321.

The thermal conductivity measuring device 300 can measure temperature changes of the first and second structures 310 and 320 and the first and second stages 350 and 360 several times while changing a direction of heat transmission. By measuring temperature changes several times, the thermal conductivity measuring device 300 can more precisely measure thermal conductivity of the sample 301.

Figure 6:
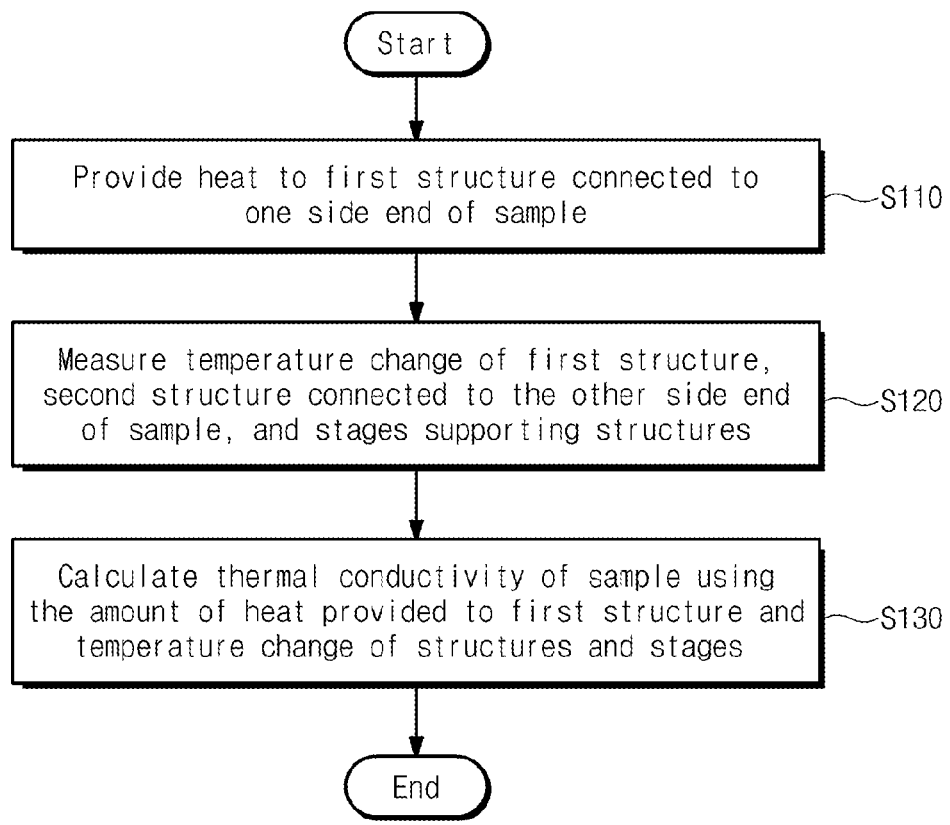
FIG. 6 is a flow chart illustrating a thermal conductivity measuring method in accordance with some embodiments of the inventive concept.

FIG. 6 is a flow chart illustrating a thermal conductivity measuring method in accordance with some embodiments of the inventive concept.

In a step S110, heat is provided to a first structure connected to one side end of a sample of which thermal conductivity is to be measured. A heat source providing heat to the first structure may be an external heat source located outside the first structure or may be an internal heat source located inside the first structure.

In a step S120, temperatures of the first structure and a second structure connected to the other side end of the sample are measured. Also, temperatures of first and second stages supporting the first and second structures respectively are measured.

In a step S130, thermal conductance and thermal conductivity of the sample are calculated using the amount of heat stored in the first structure and the temperatures measured in the step S120. The thermal conductance and thermal conductivity of the sample can be calculated using the mathematical formulas 1 through 12 described above.

Since the thermal conductivity measuring method of FIG. 6 considers not only temperature changes of the first and second structures but also a temperature change due to thermal conductivity of the first stage, reliability of measurement may become high.

Since the thermal conductivity measuring device and the thermal conductivity measuring method of the inventive concept correct a temperature change of a stage due to heat transmission emitted from the stage considering a measurement environment, reliability of measurement may be improved.

The above-disclosed subject matter is to be considered illustrative, and not restrictive, and the appended claims are intended to cover all such modifications, enhancements, and other embodiments, which fall within the true spirit and scope of the inventive concept. Thus, to the maximum extent allowed by law, the scope of the inventive concept is to be determined by the broadest permissible interpretation of the following claims and their equivalents, and shall not be restricted or limited by the foregoing detailed description.

What is claimed is:

1. A thermal conductivity measuring device comprising:
   a first structure which is connected to one side end of a sample and receives heat from a first heat source;
   a second structure which is connected to the other side end of the sample and receives heat from a second heat source;
   a first stage connected to the first structure while supporting the first structure;
   a second stage connected to the second structure while supporting the second structure;
   a connection unit connected between the first stage and the second stage; and
   a measuring unit measuring temperatures of the first and second structures and the first and second stages,
   wherein the measuring unit calculates thermal conductivity of the sample using the measured temperatures of the first and second structures and the first and second stages, and the amount of heat provided from the first and second heat sources.

2. The thermal conductivity measuring device of claim 1, wherein the measuring unit comprises a thermister.

3. The thermal conductivity measuring device of claim 1, wherein the first heat source and the second heat source are selectively operated.

4. The thermal conductivity measuring device of claim 3, wherein the measuring unit measures temperatures of the first and second structures and the first and second stages several times in response to operations of the first heat source and the second heat source.

\* \* \* \* \*